United States Patent [19]

Buksa

[11] Patent Number: Plant 6,760

[45] Date of Patent: Apr. 25, 1989

[54] GRAPEVINE, "TUDOR PREMIUM RED"

[75] Inventor: John A. Buksa, Delano, Calif.

[73] Assignee: Dan Tudor & Sons, Delano, Calif.

[21] Appl. No.: 140,662

[22] Filed: Jan. 4, 1988

[51] Int. Cl.[4] ..... A01H 5/03

[52] U.S. Cl. ..... Plt./47

[58] Field of Search ..... Plt./47

*Primary Examiner*—Robert E. Bagwill

*Attorney, Agent, or Firm*—Worrel & Worrel

[57] ABSTRACT

A new and distinct grapevine denominated varietally as Tudor Premium Red generally resembling the Emperor Grapevine (unpatented), but characterized as to novelty by producing grapes which are mature for harvesting and shipment approximately September 10 to September 17 at Delano, Calif., and which furthermore produce berries which are substantially seedless and which have an attrractive red color.

1 Drawing Sheet

BACKGROUND OF THE NEW VARIETY

The present invention relates to a new and distinct variety of grapevine denominated varietally as "Tudor Premium Red" and more particularly to a grapevine which is somewhat similar in physical characteristics to the Emperor Grapevine (unpatented) from which it was discovered as a sport, but from which it is distinguished as to novelty in its production of a red, substantially seedless berry, which is mature for commercial harvesting and shipment approximately ten to fourteen days earlier than the fruit produced by the Emperor Grapevine and which is otherwise distinguishable from the Emperor Grapevine by producing berries which have a more firm and crisp fruit texture than those berries produced by the Emperor Grapevine.

The Emperor Grapevine (unpatented) is well known as one of the best of the late bearing grapevines. As a general matter, the berries produced by the Emperor Grapevine have a desirable color and store and ship well when refrigerated. Moreover, the berries produced by the Emperor Grapevine are of a seeded type, that is, the variety's berries have from two to four well developed seeds per berry. These and other characteristics have placed the Emperor Grapevine in an important position with respect to the late marketing of grapes.

As noted above, the grapevine of the new variety is noteworthy in its production of berries that are mature for commercial harvesting approximately September 10–17, which is about ten to fourteen days earlier than the Emperor Grapevine, and which further produces an almost seedless red berry, that is a berry which contains only soft immature seed traces. Moreover, the subject variety when treated with standard cultural practices including girdling and the application of gibberellic acid produces berries which do not contain any evidence of seeds at all, as compared and contrasted with the Emperor Grapevine (unpatented), which produces berries which contain well developed seeds.

ORIGIN AND ASEXUAL REPRODUCTION OF THE NEW VARIETY

The present variety of grapevine was discovered in 1976 by the inventor, as a sport, growing in a commercial Emperor vineyard which is on the Jasmine Ranch, which is located on Woollemes Avenue in Delano, Calif. The applicant noted that the sport had several desirable traits and thereafter observed it for several years prior to a full recognition of all of its numerous characteristics. The applicant in 1980 asexually reproduced the instant grapevine by taking cuttings of the original sport and growing them to maturity at a commercial vineyard which was located at the southeast corner of Woollemes and Wallace Avenues in Delano, Calif. The pomological characteristics of the grapevines resulting from this first asexual reproduction have been continually observed by the applicant and it has subsequently been determined that they are identical to that of the original sport. The first evaluation of the instant grapevine was conducted in 1986 and a subsequent evaluation was conducted in 1987.

BRIEF DESCRIPTION OF THE DRAWINGS

The accompanying drawing is a color photograph of two bunches of grapes of the subject variety, the one on the left of the photograph showing a natural cluster of grapes sufficiently mature for harvesting and shipment, and the cluster positioned on the right of the photograph has been treated with normal cultural practices including girdling and an appropriate application of gibberellic acid, the right cluster of grapes also being sufficiently mature for harvesting and shipment; several leaves showing their dorsal and ventral coloration; a typical section of vine; and several berries halved in various planes to display the flesh color thereof, all of the instant variety.

DETAILED DESCRIPTION

Referring more specifically to the pomological details of this new and distinct variety of grapevine, the following has been observed under the ecological conditions prevailing at a vineyard which is located near the southeast corner of Woollemes and Wallace Avenues in Delano, Calif. with due regard for cultural practices.

All major color code designations have been enumerated by reference to the Dictionary of Color by Maerz and Paul, Second Edition, published in 1950. Common color names are also employed occasionally.

VINE

Size:

*Generally.*—Large.

Form: Upright, dense and tender; the subject variety was bilateral cordon trained and spur pruned.

Vigor: Vigorous.

Productivity: Variable, productive to very productive. The subject variety produces approximately 26 to 30 clusters per vine. It has been further determined that nearly all buds are fruitful, therefore the subject variety has a potential for producing a large crop. As a general matter only one cluster per shoot was produced. Occasionally two clusters per shoot were observed, however, the second cluster was always smaller in overall size.

Trunk:

*Size.*—Generally — medium to large; stocky.

*Trunk diameter.*—Variable, approximately 7 to 9.2 cm.; average trunk diameter is approximately 8.2 cm. at the point of cordon branching. The bilateral cordon training and spur pruning of the subject variety produced vines having approximately 14 to 18 arms per vine and one spur per arm.

*Bark.*—Texture — loose and shreddy.

Canes:

*Size.*—Average.

*Numbers.*—Numerous.

*Diameter.*—Medium; the cane diameter is variable, approximately 9.1 to 13.2 mm., the average cane diameter is approximately 10.7 mm.

*Color.*—Mature canes — brown, (15-E-12).

*Form.*—Straight.

*Nodes — generally.*—Present.

*Nodes — size.*—Enlarged.

*Internodes — size.*—Average.

*Internode length.*—Approximately 11 to 15 cm.; average length is approximately 12.9 cm.

*Tendrils — position.*—Intermittent; the variety displays a typical vinifera pattern.

*Tendrils — thickness.*—Average.

*Tendril length.*—Variable, medium to long; approximately 7.6 cm. through 13.9 cm.; average length is approximately 10.7 cm.

*Tendrils — form.*—Trifurcated, although occasionally bifurcated tendrils may be found.

*Tendrils — texture.*—Smooth.

*Tendrils — numbers.*—Abundant.

Flowers:

*Generally.*—Fertile with upright stamens.

*Date of bloom.*—Generally — medium to late as compared with the other varieties. The date of bloom in 1987 was observed on May 9 and 10. The date of bloom is approximately two or three days after the Emperor variety of grapevine which has a date of bloom which is considered medium to late. On May 9, 1987 approximately 80% of the clusters were in full bloom while 10% were in a pre-bloom stage and the remaining 10% were at a berry-set stage. The stamens were erect and displayed good amounts of viable pollen. The date of bloom of May 9 or 10 may be approximately seven to ten days early inasmuch as 1987 was considered an early year.

LEAVES

Size:

*Generally.*—Medium to large.

*Average length.*—Approximately 11.7 cm.

*Average width.*—Approximately 15.7 cm.

*Thickness.*—Medium.

*Form.*—Generally — roundish.

*Color — dorsal surface.*—Medium green, (23-J-7) [pg. 69].

*Color — ventral surface.*—Pale green, (23-J-5) [pg. 69].

*Texture — dorsal surface.*—Average, semi-glossy.

*Texture — ventral surface.*—Hairy.

*Lobes.*—Numbers — variable, generally five-lobed leaves were found although occasionally a three-lobed leaf would be discovered.

*Terminal lobe.*—Form — obtuse.

*Petiolar sinus — depth.*—Deep.

*Petiolar sinus — width.*—Wide.

*Petiolar sinus — shape.*—The petiolar sinus has a characteristically wide V or U-shape.

*Basal sinus.*—Shallow, and narrow.

*Lateral sinus.*—Deep, and of average width.

*Marginal form.*—Dentate.

*Teeth.*—Generally — medium in size; average, to narrow in width.

FRUIT

Maturity when described: Ripe for commercial harvesting and shipment; the ripening date of the subject variety is affected by the climatic conditions in the San Joaquin Valley of Central California. The 1987 growing season was considered an early season, and therefore the instant variety of grapevine was mature for harvesting and shipment before Sept. 1, 1987. However, the anticipated ripening date during an average season is estimated to be approximately September 10 through 17. The ripening date is medium to late as compared with other varieties.

Storage quality: Good.

Shipping quality: Good.

Cluster:

*Generally.*—The cluster of the subject variety is hereinafter described as it would be observed in its natural state, and further as it would be observed after treating it with normal cultural practices which include girdling, tipping, and applying predetermined amounts of gibberellic acid.

*Size.*—Generally — large; natural cluster weight — approximately 1060 grams to 1935 grams, with an average cluster weight of approximately 1431.2 grams. Treated cluster weight — approximately 628 to 1518 grams, with an average treated cluster weight of approximately 1991 grams.

*Length.*—Generally — medium to long.

*Natural cluster length.*—Approximately 33 to 44.5 cm.; average length of a natural cluster is approximately 38.9 cm. As part of the various cultural manipulations performed by the inventor, the clusters are tipped and thinned. Therefore, the length of a treated cluster has been altered.

*Cluster form.*—Broad and tapering. Medium and well filled but not compact. This parameter does not appear to be affected by cultural; practices.

*Peduncle — length.*—Long, approximately 5.6 cm. to 11.5 cm.; average length — approximately 8.04 cm. The peduncle length is not affected by the cultural practices set forth above.

*Peduncle — thickness.*—Medium to thick; approximately 4.3 to 7.0 mm. in natural vines; average thickness approximately 5.4 mm. The peduncle thickness is affected by the cultural practices; peduncle thickness — treated vines — approximately 3.4 to 7.6 mm.; average peduncle thickness for a treated vine is approximately 6.0 mm.

*Pedicle — length.*—Short, approximately 7.5 mm.

*Pedicle — diameter.*—Slender, approximately 1.3 mm. The pedicle length, and diameter, set forth above were not noticeably affected by the cultural practices which included girdling and the application of predetermined amounts of gibberellic acid.

*Warts.*—Numbers — few.

*Brush — length.*—Short.

*Brush — color.*—Variable, white or yellow.

Berry:

*Shells.*—Generally — strong to medium adherent shells.

*Size.*—Large.

*Berry length.*—Natural vines — approximately 2.2 cm.; treated vines — approximately 2.4 cm.

*Berry diameter.*—Natural vines — approximately 1.9 cm.; treated vines — approximately 2.0 cm.

*Berry weight.*—Natural vines — approximately 4.4 grams; treated vines — approximately 5.7 grams.

*Uniformity.*—Variable on clusters procured from natural vines, however, increased uniformity is apparent on clusters gathered from treated vines.

*Berry color.*—Red, (56-L-7) [pg. 135]; the color of the berries is somewhat variable ranging from 56-L-5 to 56-L-8, most of the berries, however, display the red color which is most closely similar to (56-L-7).

*Bloom.*—Average.

*Skin — thickness.*—Medium.

*Skin — texture.*—Tender; the skin adheres to the pulp.

Flesh:

*Appearance.*—Generally — white, and translucent.

*Texture.*—Medium, tender, and crisp.

*Juice production.*—Average to juicy. The juice of the subject variety is clear and sweet.

*Flavor.*—Neutral.

*Quality.*—Very good; crisp.

Seeds: The Tudor Premium Red variety of grapevine is substantially seedless, that is, natural vines produce berries which have one or two seed traces. The seed traces which are found in these berries, are not otherwise noteworthy, inasmuch as they are soft. They are however visually detectable. It has been determined that seed traces were substantially undetectable in the berries which are produced from vines which were treated with the standard cultural practices which include girdling and the application of predetermined amounts of gibberellic acid.

Use: Dessert and fresh market for both local and long distance markets.

Although the new variety of grapevine possesses the described characteristics as a result of the growing conditions prevailing in Delano, Calif., it is to be understood that variations of the usual magnitude and characteristics incident to growing conditions, fertilization, pruning and pest control are to be expected.

Having thus described and illustrated my new variety of grapevine, I claim:

1. A new and distinct variety of grapevine to be denominated varietally as Tudor Premium Red substantially as illustrated and described which is characterized principally as to novelty by its production of a red colored, substantially seedless berry which is mature for harvesting and shipment approximately September 10 through 17, in Delano, Calif., said grapevines maturing in approximately the same season as the Emperor Grapevine (unpatented) with which it is most closely similar, but from which it is distinguished as to novelty by producing berries which are mature for commercial harvesting and shipment approximately ten to fourteen days earlier than the Emperor variety of grapevine, and has a fruit texture which is more firm and crisp than the fruit produced by the Emperor Grapevine.

* * * * *

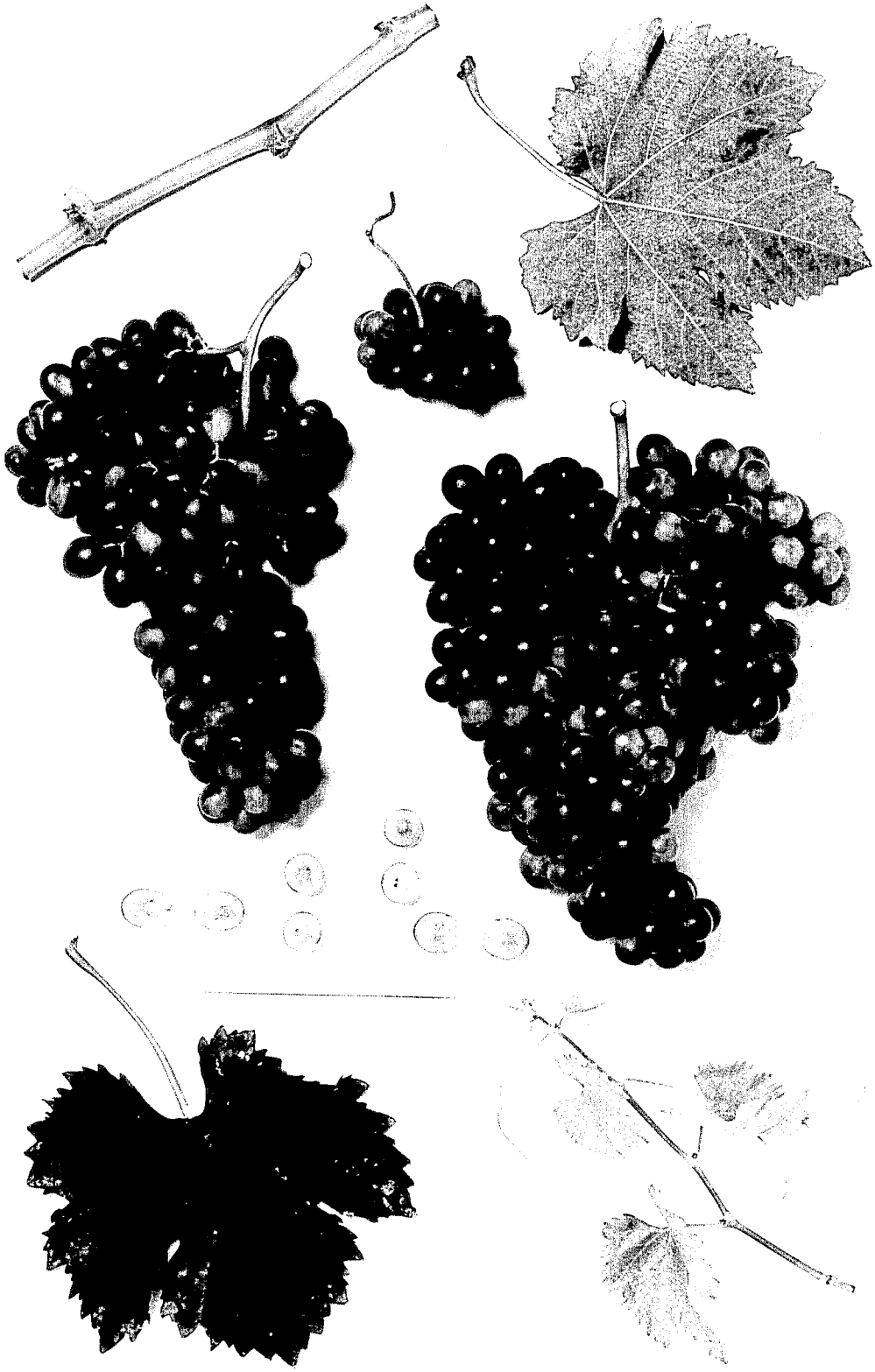

UNITED STATES PATENT AND TRADEMARK OFFICE

CERTIFICATE OF CORRECTION

PATENT NO. : Plant 6,760

DATED : April 25, 1989

INVENTOR(S) : John A. Buksa

It is certified that error appears in the above-identified patent and that said Letters Patent is hereby corrected as shown below:

Column 4, Line 7

Insert ---,--- between the words generally and five

Column 4, Line 59

Delete ";" between the words cultural and practices

Signed and Sealed this

Twelfth Day of December, 1989

*Attest:*

JEFFREY M. SAMUELS

*Attesting Officer* *Acting Commissioner of Patents and Trademarks*